United States Patent
Reho et al.

(10) Patent No.: US 7,324,841 B2
(45) Date of Patent: Jan. 29, 2008

(54) SENSOR ARRANGEABLE ON THE SKIN

(75) Inventors: Akseli Reho, Kankaanpää (FI); Elina Välimäki, Tampere (FI); Seppo Nissilä, Oulu (FI); Ilkka Heikkilä, Oulu (FI)

(73) Assignee: Polar Electro OY, Kempele (FI)

( * ) Notice: Subject to any disclaimer, the term of this patent is extended or adjusted under 35 U.S.C. 154(b) by 214 days.

(21) Appl. No.: 10/468,440

(22) PCT Filed: Feb. 18, 2002

(86) PCT No.: PCT/FI02/00132

§ 371 (c)(1),
(2), (4) Date: Oct. 14, 2003

(87) PCT Pub. No.: WO02/071935

PCT Pub. Date: Sep. 19, 2002

(65) Prior Publication Data

US 2004/0138546 A1    Jul. 15, 2004

(30) Foreign Application Priority Data

Feb. 19, 2001  (FI) .................................. 20010311

(51) Int. Cl.
*A61B 5/04*  (2006.01)
*A61B 5/02*  (2006.01)

(52) U.S. Cl. ...................... 600/382; 600/386; 600/388; 600/389; 600/390; 600/502

(58) Field of Classification Search .............. 600/382, 600/386, 388, 389, 390, 502
See application file for complete search history.

(56) References Cited

U.S. PATENT DOCUMENTS

| | | | |
|---|---|---|---|
| 3,954,100 A * | 5/1976 | Sem-Jacobsen | 600/393 |
| 4,729,377 A | 3/1988 | Granek et al. | |
| 5,450,845 A | 9/1995 | Axelgaard | |
| 5,624,736 A | 4/1997 | DeAngelis et al. | |
| 5,947,897 A * | 9/1999 | Otake | 600/372 |
| 6,263,226 B1 * | 7/2001 | Axelgaard et al. | 600/391 |
| 6,381,482 B1 * | 4/2002 | Jayaraman et al. | 600/388 |

FOREIGN PATENT DOCUMENTS

| | | |
|---|---|---|
| GB | 2 150 332 A | 6/1985 |
| JP | 2000-000221 | 1/2000 |
| WO | 99/64657 | 12/1999 |
| WO | 01/01855 A1 | 1/2001 |
| WO | 01/02052 A2 | 1/2001 |
| WO | 02/30279 A1 | 4/2002 |

* cited by examiner

*Primary Examiner*—Lee S. Cohen
(74) *Attorney, Agent, or Firm*—Buchanan Ingersoll & Rooney PC

(57) ABSTRACT

The invention relates to a sensor (42) placed on the skin, which can advantageously be integrated in a garment and has a contact layer in contact with the skin containing conductive fibres for receiving signals and a moisture retentive moisture layer (41) on top of the contact layer.

10 Claims, 2 Drawing Sheets

SENSOR ARRANGEABLE ON THE SKIN

TECHNOLOGICAL BACKGROUND

The invention relates to a sensor placed on the skin, which can be used for metering the pulse of humans, for instance.

Sensors attached to the skin, for instance are used in pulsometers. The operation is based on the feature of the sensor comprising a contact layer whose electric conductivity varies under the pressure exerted on it. In this manner, this layer emits a signal corresponding to the pulse. The sensor is often connected to a strip, which can be tightened around the chest. A separate sensor can also be attached to the skin by means of tape or elastic bands. Separate sticker tapes can also be used for fastening the sensor.

Strips, tapes, bands, sticker tapes and similar are often unpleasant in use, because they tend to give a sensation of pressure and to harm metering or other movements in general. In many cases, there are problems in keeping the sensor in position. Thus, for instance, to keep a band in place in hard physical exercise, separate tops and similar garments have to be worn on top of the strip in order to achieve adequate and reliable contact between the sensor and the skin.

The contact layer should be brought into tight contact with the skin for the measurements to be sufficiently reliable. To ensure skin contact, liquids such as water or grease can be used between the contact layer and the skin. After the measurement, the sensor and the skin often need to be cleaned separately to avoid any hygienic inconveniences caused by the use of a sensor.

GENERAL DESCRIPTION OF THE INVENTION

The sensor in accordance with the invention comprises a contact layer including conductive fibres, and a moisture layer for retaining moisture on top of the contact layer. The moisture layer may be an impervious, substantially moisture proof seal layer or an absorption layer with efficient moisture absorption. Data to be measured are collected on the skin with the aid of the contact layer. The contact layer may consist e.g. of a fabric-like layer, which readily adapts to the skin surface. The moisture layer retains secretory products from the skin, such as moisture and electrolytes. This enhances the contact between the skin and the contact layer and increases the electric conductivity of the contact layer. The moisture layer may also be made of a fabric-like material adapting to the skin. The seal layer prevents transpiration secreted at the contact layer from escaping from the contact layer. The seal layer may be made e.g. of a waterproof or non-respiring fabric, or a film-like material, such as suitable plastic, e.g. silicone plastic or rubber or a laminate layer. The absorption layer efficiently absorbs perspiration secreted at the contact layer. The absorption layer may comprise e.g. moisture absorbing fibres.

The sensor of the invention can be given a textile-like embodiment. It can thus be shaped in the way of a fabric soft and adaptable on the skin. It can also be given a very small weight, being thus easy to use. The fabric may also be mesh-like or film-like.

The sensor can be integrated in a garment, being thus especially pleasant and practical in use. The conductive fibres in the contact layer can be sewn into the fabric surface or they can be knitted or woven directly in the fabric texture. Knitted or woven conductive fibres are not necessarily distinguished at all in the garment, and in addition, they may enhance the elasticity and strength properties of the product.

The moisture layer can also be sewn in the fabric, or connected to the fabric by means of a sticker tape, for instance. The moisture layer can also be provided by being knitted or woven in the fabric texture. In this manner, a light sensor is obtained, whose overall design is adaptable to the skin and does not exert any pressure on the skin.

A sensor that is integrated in a garment provides extremely good comfort of use. It is rapidly attached. It is also pleasant to wear, because it does not press on the chest or the point of attachment. It is also simple to use, because the sensor does not need to be wetted separately, for instance.

When the sensor is made of materials that can be wet cleaned, it can be washed together with other laundry. This yields higher hygienic in use, because the sensor is easier and more efficiently cleaned.

The sensor can typically be placed in the chest area of a garment, or the measurement can also be made e.g. in the area of the neck or the wrists. The sensor can be combined with various pieces of clothing, such as an undershirt, bras, a top, a turtleneck, a headband, a wristband or any other garment.

In one embodiment of the invention, at least part of the sensor can be placed e.g. in a sock, a glove, a trouser leg or a shirt arm or shoulder area, and at least a second part of the sensor (counter-piece) can be placed the other sock, the other glove, the other trouser leg, the other shirt arm or in the other shoulder area. In this manner, the variable to be measured can be measured e.g. in the lea muscles by using two socks or trouser legs of the invention, and in the area between the arms, such as the biceps or the breast muscles by using two gloves or shirt arms of the invention.

Using a garment including the sensor of the invention, data to be measured can be collected to determine at least one of the following data: pulse, respiratory frequency, electric conductivity of the skin, fat percentage, liquid balance, electrocardiography (allowing monitoring of the electric function of the heart muscle) and electromyography (electric muscle examination).

The sensor of the invention can be solidly or detachably connected to a transmitter. The connection can be made e.g. by means of conductive threads, press studs, conductive sticker tapes and a magnet, or combinations of these. The transmitter can be placed e.g. in the hem, neck or seams of a garment. The transmitter can be solidly attached to the sensor, provided that it can be appropriately cleaned, by washing, for instance. The transmitter can also be a sticker tape or a headband, for instance.

The receiver can be mounted at the user's wrist, for instance. It can also be attached directly to a transmitter provided in the garment.

The conductive fibres in the sensor of the invention can be made e.g. of metal-coated polymer.

The moisture layer of the sensor preferably surrounds the contact layer so as to fit against the skin around the contact area.

Besides humans, the sensor of the invention can be placed on the skin of an animal. It should also be noted that the sensor of the invention can be an electrode, and then the actual sensor and the part for analyzing a physical variable can be integrated in a transmitter attached to a press stud, for instance.

DETAILED DESCRIPTION OF THE INVENTION

A number of embodiments of the invention are described in detail below with reference to the accompanying drawings.

Figure 1:
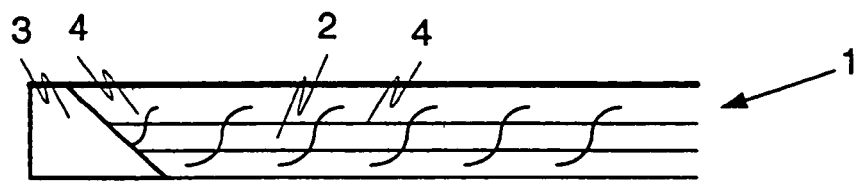
FIG. 1 shows the design of a sensor of the invention.

The sensor 1 shown in FIG. 1 has a contact layer 2 made of conductive fibres 4 e.g. by weaving, knitting, twining, pressing, gluing or sewing. The second layer of the sensor is a seal layer 3 made of a non-respiring and waterproof fabric. The seal layer 3 may also be a laminated layer, for instance.

The sensor 1 is typically placed on the skin with the contact layer 2 against the skin and the seal layer 3 remote from the skin. As the sensor 1 is placed on the skin, the seal layer 3 of the sensor 1 starts collecting moisture from the skin on its lower surface. The seal layer also retains other secretory products from the skin, such as salts, within the contact layer 2. Then the skin contact and the conductive properties of the contact layer are substantially improved.

Figure 2:
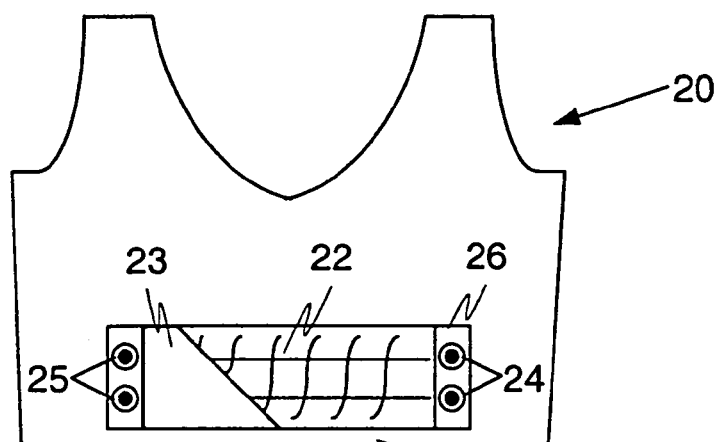
FIG. 2 shows a sensor of the invention connected to a fabric by sewing or weaving.

In FIG. 2, the contact layer 22 of the sensor 21 has been woven from conductive. fibres in a top 20, and on top of this, a non-respiring fabric has been woven to act as the seal layer 23 of the sensor. Press studs 24, 25 have been connected to the contact layer, extending from the inner layer to the outer layer in the fabric. A transmitter 26 has been connected to the press studs 24 for retransmitting signals reaching the contact layer to the receiver. A second transmitter can be connected to the press studs 25 for sending different signals from the contact layer.

Figure 3:
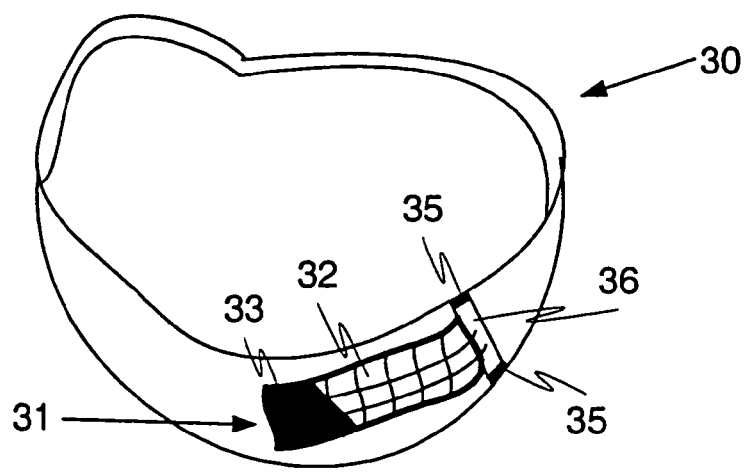
FIG. 3 shows a sensor of the invention connected to a band.

In FIG. 3, a sensor 31 has been solidly mounted in the band 30, comprising a contact layer 32 woven from conductive fibres and a seal layer 33 made of a non-respiring fabric. A transmitter 36 equipped with conductive sticker tapes 35 has been connected to the band. The conductive sticker tape 35 has been connected to the contact layer 32 for collecting data to be measured. During physical exercise, the band 30 of the invention can be mounted e.g. at the one wrist of the person and the receiver at his/her other wrist.

Figure 4:
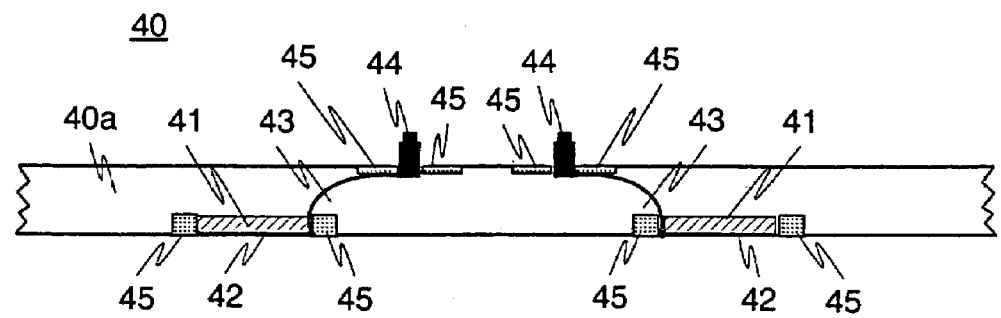
FIG. 4 shows a sensor arrangement of the invention in cross-section.

FIG. 4 shows a sensor arrangement 40 of the invention in cross-section, where the sensors are integrated in a garment member 40a, such as e.g. a belt, a string or a band. The actual at least one sensor 42 including its contact and seal layers is integrated in the surface of the garment member 40a with a seal layer 41 provided on the side opposite to the sensor part 42 placed in contact with the skin, the seal layer being of any suitably moisture-absorbing material, such as rubber or plastic. However, the moisture layer 41 is preferably a laminate layer.

A physical variable measured on the skin, such as voltage or current, for instance, is conducted by means of a conductor material 43 typically insulated from the sensor part 42 to the means 44, the emitter being connected to these means. The sensors 42 included in the garment member 40a and their contact layers, and also the means 44 made of conductive material, have mutual electric insulation with some suitable insulating material 45 to avoid short-circuiting between the different sensors and the means 44. The insulating material 45 used can be any material known to those skilled in the art, such as e.g. plastic, rubber, glue or fabric. In the embodiment shown in FIG. 4, the means 44 are surrounded with an insulating material 45 insulating from the garment member 40a, and so are the sensors 42. In one embodiment, the sensors 42 can be coated or moulded, except for the contact layer in contact with the skin, in order to prevent short-circuiting of the insulating material.

Figure 5:
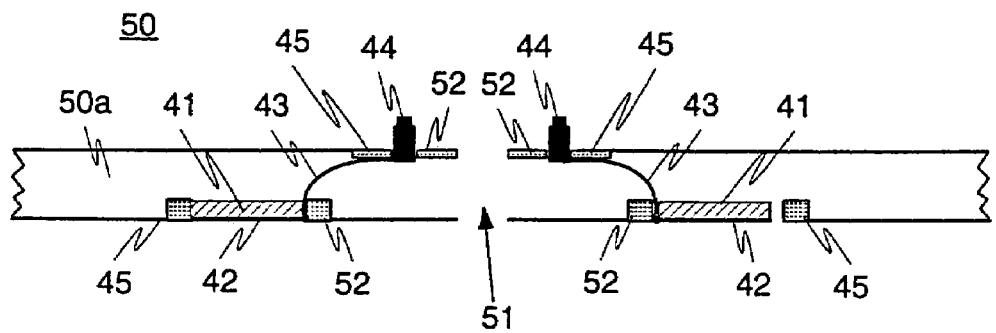
FIG. 5 shows a sensor arrangement of the invention in cross-section.

FIG. 5 shows a cross-section of a sensor arrangement 50 similar to the one shown in FIG. 4, where the sensors are integrated in a garment member 50a, such as e.g. a belt, a strip or a band. The garment member 50a in the sensor arrangement 50 shown in FIG. 5 is characterised by the fact that the garment member 50a is sectioned at least at one point 51. The sectioning point 51 may be e.g. the belt joint or the lap, hem or other section of a shirt/coat. The sectioning point 51 is preferably positioned so as to separate at least one pair of sensors 42 and/or one pair of means 44. In that case, it will not be necessary to provide insulation 52 around the means 44 and the sensors 42.

Figure 6:
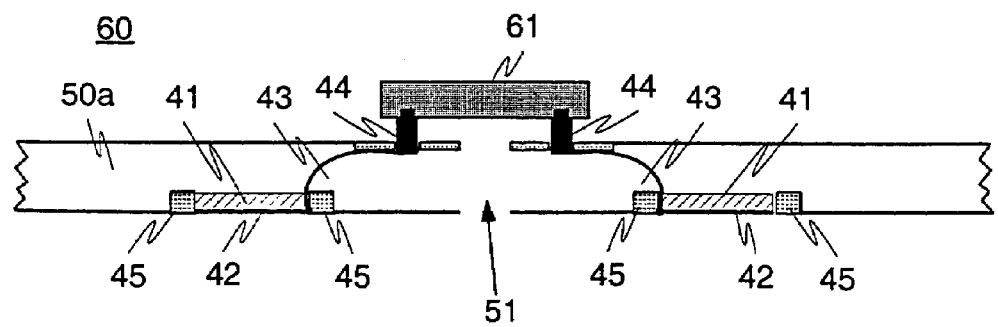
FIG. 6 shows a sensor arrangement of the invention in cross-section.

FIG. 6 shows a cross-section of a sensor arrangement 60 similar to the one shown in FIG. 5, where a transmitter 61 has been connected between means 44, such as press studs, electrically conductive sticker tapes or similar. The transmitter 61 may comprise means for analyzing and/or sending variables measured by the sensors 42 to a receiver, which may be e.g. a receiver kept at the wrist or integrated in a watch. The transmitter 61 can of course be used in connection with other garments of the invention, such as those shown in FIGS. 2-5, and to other garments mentioned in the disclosure and similar garments, in which the sensor arrangement of the invention has been integrated.

The invention claimed is:

1. A sensor adapted to be integrated in a garment so as to be placed in contact with skin of a user during use of the garment, said sensor comprising:
   a contact layer including conductive fibers to be placed in contact with the skin for receiving signals, and
   a moisture retentive layer on top of the contact layer for retaining secretory products from the skin thereby enhancing the contact between the skin and the contact layer, and increasing the electric conductivity of the contact layer.

2. A sensor as defined in claim 1, wherein the moisture retentive layer is a seal layer substantially impervious to moisture.

3. A sensor as defined in claim 2, wherein the seal layer is made of fabric, a film-like material or laminate.

4. A sensor as defined in claim 1, wherein the contact layer is made of fabric.

5. A sensor as defined in claim 1 in combination with a garment, wherein the garment is at least one of the following garment: a shirt, a coat, a top, a girdle, a bra, a wrist strip, a headband, a belt, a band, a sock, a pair of trousers or a glove.

6. A sensor and garment in combination as defined in claim 5, wherein the sensor and the garment are arranged to be cleaned together.

7. A sensor as defined in claim 1, wherein the sensor is associated with a transmitter for transmitting a signal received by the contact layer from the skin.

8. A sensor as defined in claim 1, further comprising a short-circuit preventing insulating arrangement surrounding the other elements of the sensor, wherein the insulating arrangement is at least one of the following insulating arrangements: rubber, plastic fabric, glue and an opening.

9. A garment, comprising:

a garment member, a sensor mounted on the garment member and adapted to be placed in contact with skin, said sensor comprising a contact layer containing conductive fibers to be placed in contact with the skin for receiving signals, and a moisture retentive layer on top of the contact layer for retaining secretory products from the skin thereby enhancing the contact between the skin and the contact layer, and increasing the electric conductivity of the contact layer.

10. A method for making measurements by means of a sensor integrated in a garment so as to be placed in contact with skin of a user during use of the garment, said sensor comprising a contact layer including conductive fibers to be placed in contact with the skin for receiving signals, and a moisture retentive layer on top of the contact layer and increasing the electric conductivity of the contact layer; the method comprising integrating the sensor in the garment and receiving signals from the contact layer for making the measurements.

* * * * *